United States Patent
Scatterday

(10) Patent No.: US 8,807,140 B1
(45) Date of Patent: Aug. 19, 2014

(54) ELECTRONIC CIGARETTE CONFIGURED TO SIMULATE THE TEXTURE OF THE TOBACCO ROD AND CIGARETTE PAPER OF A TRADITIONAL CIGARETTE

(71) Applicant: Mark Scatterday, Scottsdale, AZ (US)

(72) Inventor: Mark Scatterday, Scottsdale, AZ (US)

(73) Assignee: Njoy, Inc., Scottsdale, AZ (US)

( * ) Notice: Subject to any disclaimer, the term of this patent is extended or adjusted under 35 U.S.C. 154(b) by 0 days.

(21) Appl. No.: 13/861,132

(22) Filed: Apr. 11, 2013

Related U.S. Application Data

(60) Provisional application No. 61/693,219, filed on Aug. 24, 2012.

(51) Int. Cl.
*A24F 47/00* (2006.01)

(52) U.S. Cl.
USPC .................. 131/273; 131/270; 131/365

(58) Field of Classification Search
None
See application file for complete search history.

(56) References Cited

U.S. PATENT DOCUMENTS

| | | | |
|---|---|---|---|
| 2,545,851 A | 3/1951 | Kardos | |
| 2,702,033 A | 2/1955 | Pardeman | |
| 3,789,840 A | 2/1974 | Rosenblatt | |
| 4,587,982 A * | 5/1986 | Adams et al. | 131/336 |
| 4,756,318 A * | 7/1988 | Clearman et al. | 131/359 |
| 5,131,415 A * | 7/1992 | Munoz et al. | 131/298 |
| 2002/0005207 A1* | 1/2002 | Wrenn et al. | 131/194 |
| 2003/0015111 A1* | 1/2003 | Rizika et al. | 101/416.1 |
| 2003/0089377 A1* | 5/2003 | Hajaligol et al. | 131/365 |
| 2004/0134631 A1 | 7/2004 | Crooks et al. | |
| 2008/0131641 A1* | 6/2008 | Hannington | 428/41.8 |
| 2009/0162294 A1 | 6/2009 | Werner | |
| 2010/0147317 A1* | 6/2010 | Fallon | 131/332 |
| 2010/0163062 A1* | 7/2010 | Atchley et al. | 131/119 |
| 2011/0315153 A1* | 12/2011 | Fiebelkorn et al. | 131/284 |
| 2012/0186594 A1* | 7/2012 | Liu | 131/329 |
| 2013/0061861 A1* | 3/2013 | Hearn | 131/329 |
| 2013/0192622 A1* | 8/2013 | Tucker et al. | 131/329 |

OTHER PUBLICATIONS

E-Cigarette Forum, May 2012, http://www.e-cigarette-forum.com/forum/modder-accessories-supplier-forum/177608-griffs-leather-mod-holsters-45.html.*

* cited by examiner

*Primary Examiner* — Richard Crispino
*Assistant Examiner* — Eric Yaary
(74) *Attorney, Agent, or Firm* — Weiss & Moy, P.C.; Veronica-Adele R. Cao

(57) ABSTRACT

The present disclosure generally relates to electronic cigarette components. As will be disclosed, an electronic cigarette may have a flexible conduit, texture layer, and outer wrapper. The texture layer may be constructed of synthetic or organic material that, together with the outer wrapper will simulate the texture of the tobacco rod and cigarette paper of a traditional cigarette.

13 Claims, 4 Drawing Sheets

ELECTRONIC CIGARETTE CONFIGURED TO SIMULATE THE TEXTURE OF THE TOBACCO ROD AND CIGARETTE PAPER OF A TRADITIONAL CIGARETTE

CROSS-REFERENCE TO RELATED APPLICATION

This disclosure claims priority to Provisional Application No. 61/693,219, filed on Aug. 24, 2012 in the name of the Applicant.

TECHNICAL FIELD

This disclosure generally relates to alternative smoking devices, and more particularly, to an electronic cigarette configured to simulate the texture of the tobacco rod and cigarette paper of a traditional cigarette.

SUMMARY

This summary is provided to introduce a selection of concepts in a simplified form that are further described below in the DESCRIPTION OF THE DISCLOSURE. This summary is not intended to identify key features of the claimed subject matter, nor is it intended to be used as an aid in determining the scope of the claimed subject matter.

In accordance with aspects of the present disclosure, electronic cigarette components are presented. The disclosure presents an electronic cigarette configured to simulate the texture of the tobacco rod and cigarette paper of a traditional cigarette.

In accordance with one embodiment of the present invention, an electronic cigarette configured to simulate the texture of the tobacco rod and cigarette paper of a traditional cigarette is disclosed. The electronic cigarette comprises: a texture layer disposed over components of an electronic cigarette device; and wherein the texture layer is configured to provide a surface of the electronic cigarette device that is non-smooth to the touch and that simulates a surface of a tobacco rod in a tobacco cigarette.

In accordance with one embodiment of the present invention, an electronic cigarette configured to simulate the texture of the tobacco rod and cigarette paper of a traditional cigarette is disclosed. The electronic cigarette comprises: a conduit adapted to contain components of an electronic cigarette device; an outer wrapper; a texture layer located between at least a portion of the conduit and the outer wrapper, wherein the texture layer comprises a layer of particulate; and a laminate coupled to at least a portion of an outer surface of the outer wrapper.

In accordance with one embodiment of the present invention, an electronic cigarette configured to simulate the texture of the tobacco rod and cigarette paper of a traditional cigarette is disclosed. The electronic cigarette comprises: a conduit adapted to contain components of an electronic cigarette device; an outer wrapper coupled the to the conduit, wherein the outer wrapper comprises paper having: an overlap portion along at least one long edge of an inner surface of the outer wrapper, and wherein the particulate does not contact the overlap portion; a first portion configured to simulate cigarette paper wrapped about a tobacco rod portion of a traditional cigarette; and a second portion configured to simulate a filter portion of a traditional cigarette; a layer of particulate located only between the first portion of the outer wrapper and the conduit; and a laminate coupled to only an outer surface of the second portion of the outer wrapper, wherein the second portion of the outer wrapper is coupled directly to the conduit.

BRIEF DESCRIPTION OF THE DRAWINGS

The novel features believed to be characteristic of the application are set forth in the appended claims. In the descriptions that follow, like parts are marked throughout the specification and drawings with the same numerals, respectively. The drawing figures are not necessarily drawn to scale and certain figures can be shown in exaggerated or generalized form in the interest of clarity and conciseness. The application itself, however, as well as a preferred mode of use, further objectives and advantages thereof, will be best understood by reference to the following detailed description of illustrative embodiments when read in conjunction with the accompanying drawings, wherein:

DESCRIPTION OF THE DISCLOSURE

Figure 1A:
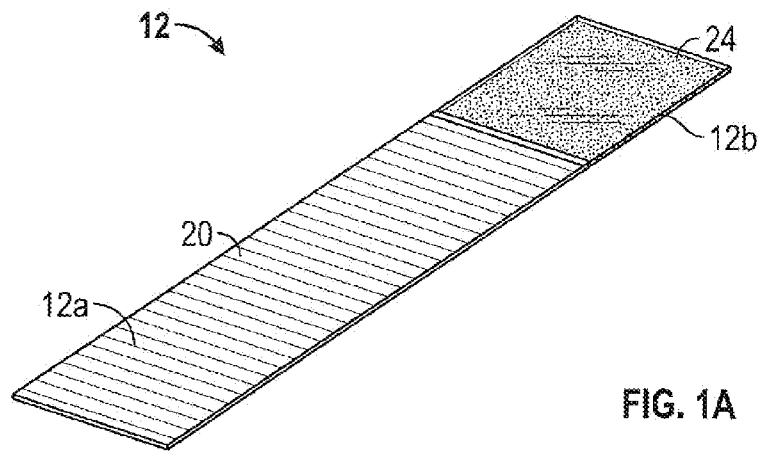
FIG. 1A is a perspective view of the outer surface of the outer wrapper of an electronic cigarette in accordance with one or more aspects of the present disclosure.

The description set forth below is intended as a description of presently preferred embodiments of the disclosure and is not intended to represent the only forms in which the present disclosure can be constructed and/or utilized. The description sets forth the functions and the sequence of steps for constructing and operating the disclosure. It is to be understood, however, that the same or equivalent functions and sequences can be accomplished by different embodiments that are also intended to be encompassed within the spirit and scope of this disclosure.

The present disclosure generally relates to electronic cigarettes. As will be disclosed, in one embodiment, an electronic cigarette 100 can have a conduit 10 for protecting its internal components, an outer wrapper 12, and a texture layer 22 that, in combination with the outer wrapper 12, simulates the texture of a traditional cigarette. A number of advantages can be provided by the electronic cigarette components described herein. The texture layer 22 and the outer wrapper 12 of the electronic cigarette 100 may together simulate the look and feel of the tobacco rod and cigarette paper of a traditional cigarette. As also discussed herein, an electronic cigarette 100 can have a conduit 10 that itself is textured, and optionally comprised of a paper type of material, for protecting its internal components and simulating the texture of a traditional cigarette. Still further, an electronic cigarette 100 can have a conduit 10 for protecting its internal components and a textured outer wrapper 12 that simulates the texture of a traditional cigarette. A number of additional advantages will become apparent from the description provided below.

Prior art alternative smoking devices can include a number of components consisting of a battery and liquid source. The battery can be a pre-charged, disposable type of device that is not rechargeable or, alternatively, a rechargeable battery. The body of prior art electronic cigarette embodiments can have a conduit that is made of metal. The metal in the device allows for sturdiness and protects the interior components, However, the metal may be cold, hard, and completely smooth, resulting in an unrealistic simulation of the look and feel of the tobacco rod and cigarette paper of a traditional cigarette.

FIGS. 1A through 6 show an electronic cigarette 100 configured to simulate the texture of the tobacco rod and cigarette paper of a traditional cigarette. In the present invention, the metal conduit may be replaced with one that is relatively flexible. The conduit 10 may be made of plastic, polyvinyl chloride (PVC), polyethylene, polypropylene, polycarbonate, paper, paper-containing, or other suitable material that is more flexible than the metal used within prior art alternative smoking devices. The conduit 10 can extend the entire length of the electronic cigarette 100. The conduit 10 can cover the internal components of the electronic cigarette which may include a vaporizer (not shown), battery (not shown), liquid source (not shown), integrated circuit (not shown), light source (not shown), and end piece 34. The conduit 10 can also cover a portion or the entirety of a filter (not shown) of the electronic cigarette 100.

Traditional cigarettes are available in multiple sizes and diameters. A "regular" size traditional cigarette typically has an outside diameter of about 8 mm. "Slim" traditional cigarettes typically have an outside diameter of about 6 mm and "wide" traditional cigarettes typically have an outside diameter of about 10 mm. In one embodiment of the present invention, the outside diameter of the electronic cigarette 100 is about 8 mm, so that it closely replicates the outside diameter of a regular sized traditional cigarette. It should be clearly understood, however, that substantial benefit may be derived from the electronic cigarette 100 having an outside diameter similar to that of a "slim" traditional cigarette or a "wide" traditional cigarette or any other desired size.

In one embodiment of the present invention, the internal components of the electronic cigarette 100 (e.g. the vaporizer, battery, liquid source, integrated circuit, and light source) are positioned within the conduit 10. The internal components may have an outside diameter slightly less than an inside diameter of the conduit 10 which would allow the internal components to be held in place by the friction that is created between the outer surface of the internal components and the inner surface of the conduit 10. For example, if the conduit 10 has an inside diameter of about 6 mm, then the outside diameter of the internal components would be slightly less than 6 mm.

Referring to FIGS. 1A, 1B, 4, 5, and 6, the outer surface 20 of the outer wrapper 12 may be configured to simulate the look and feel of the cigarette paper and filter of a traditional cigarette. For example, the outer wrapper 12 may be made of paper or any other suitable material which is textured during manufacture. Alternatively, as shown in FIGS. 2, 3, 5, and 6, the electronic cigarette 100 may also have a texture layer 22, disposed below the outer wrapper 12, which cooperates with the outer wrapper 12 to simulate the look and texture of the tobacco rod of a traditional cigarette. (As an additional alternative, the conduit 10 may itself be textured, and the need for the outer wrapper 12 and/or texture layer 22 eliminated.)

Figure 1B:
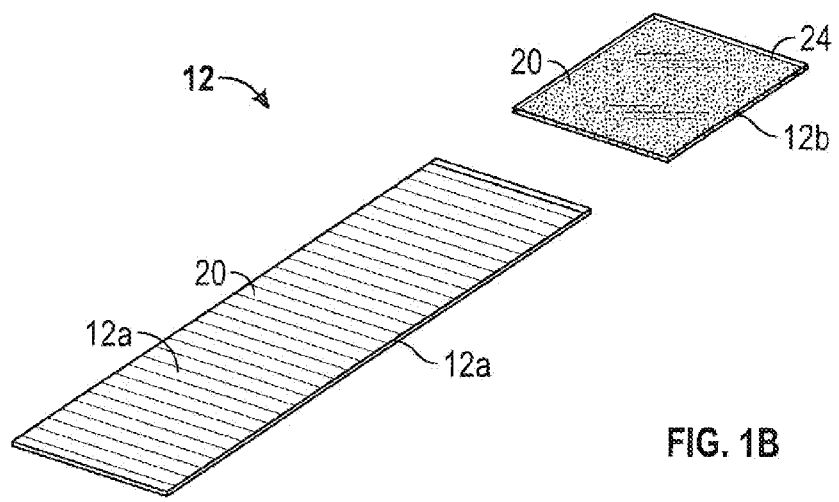
FIG. 1B is a perspective view of the outer surface of the outer wrapper of another embodiment of an electronic cigarette in accordance with one or more aspects of the present disclosure.

As shown in FIG. 1A, the outer wrapper 12 may be constructed as one piece, that may cover the entire length of the conduit 10. The outer surface 20 of a first portion 12a of the outer wrapper 12 may have the appearance of the cigarette paper wrapped about the tobacco rod of a traditional cigarette and the outer surface 20 of a second portion 12b of the outer wrapper 12 may have the appearance of the filter portion of a traditional cigarette. Alternatively, as shown in FIG. 1B, the outer wrapper 12 may be constructed as two separate portions: a first portion 12a wherein its outer surface 20 has the appearance of the cigarette paper wrapped about the tobacco rod of a traditional cigarette and second portion 12b wherein its outer surface 20 has the appearance of the filter portion of a traditional cigarette.

Figure 2:
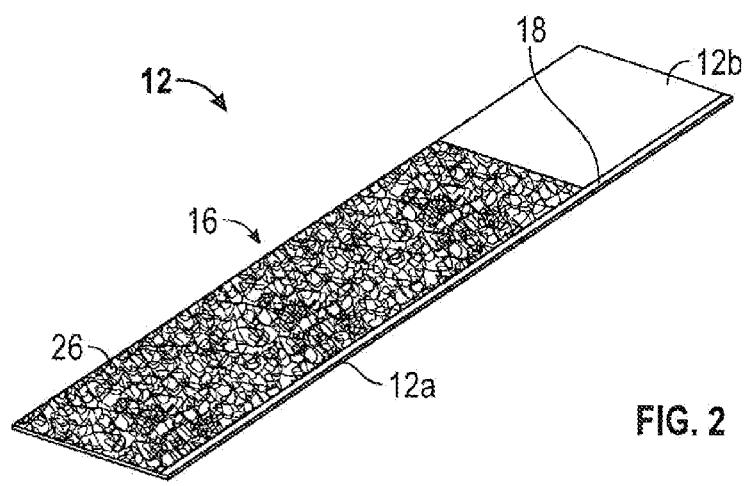
FIG. 2 is a perspective view of the inner surface of the outer wrapper of an electronic cigarette in accordance with one or more aspects of the present disclosure.
Figure 3:
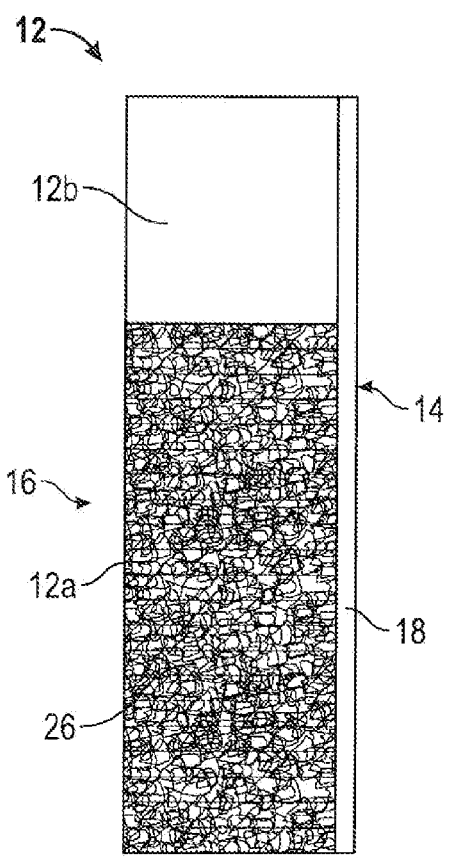
FIG. 3 is a front view of the inner surface of the outer wrapper of FIG. 2.
Figure 4:
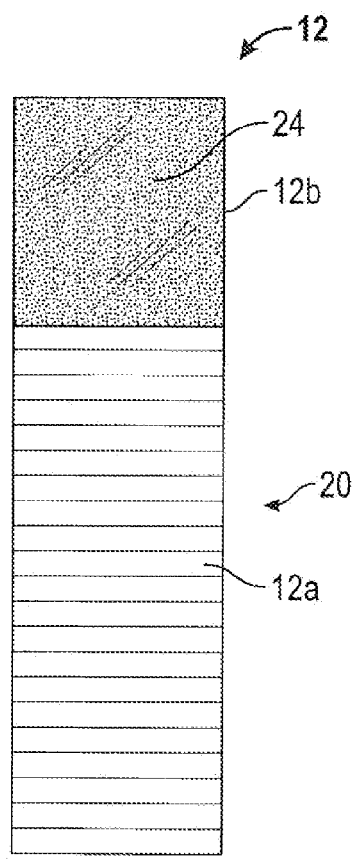
FIG. 4 is a front view of the outer surface of the outer wrapper of FIG. 1A.

According to one embodiment of the present invention shown in FIGS. 1A-4, the outer wrapper 12 and the texture layer 22 may be constructed by running the outer wrapper 12 and particulate 26 through a press. This will allow a portion of the particulate 26 to be embedded into the inner surface 16 of the outer wrapper 12, thereby creating a bumpy surface on the outer surface 20 of the outer wrapper 12. This bumpy surface simulates the bumpy texture that the tobacco rod creates on the cigarette paper of a traditional cigarette. The outer wrapper 12 and particulate 26 may be compressed into a desired thickness and an adhesive may then be applied to one or more of the particulate 26, outer wrapper 12, or conduit 10. The outer wrapper 12 could thus be integral to the texture layer 22, which in this example is comprised of the adhesive and the layer of particulate 26. Such a method of manufacture may also be utilized to fabricate a textured conduit 10, in an embodiment in which no outer wrapper 12 is provided, As shown in FIGS. 2 and 3, a portion of the inner surface 16 of the outer wrapper 12 may not be pressed with any particulate 26. This bare portion, or overlap portion 18, of the inner surface 16 of the outer wrapper 12 may be present along one long edge 14 of the outer wrapper 12. While this overlap portion 18 may not contain any particulate 26, it may contain an adhesive layer (not shown). When the outer wrapper 12 and texture layer 22 are wrapped about the conduit 10, the overlap portion 18 may then be adhered to the outer surface 20 of the other long edge 14 of the outer wrapper 12, thereby securing the outer wrapper 12 and texture layer 22 about the conduit 10. The overlap portion 18 may be about 3 mm wide to ensure secure adhesion about the conduit 10. It should be clearly understood, however, that substantial benefit may be derived from the overlap portion 18 having a different width.

Furthermore, the second portion 12b of the inner surface 16 of the outer wrapper 12 that is intended to simulate the filter portion of a traditional cigarette may not be pressed with any particulate 26. Thus, the second portion 12b of the outer wrapper 12 may be, in one embodiment, coupled directly to the conduit 10. This will help this filter portion of the outer wrapper 12 to maintain a smooth look and feel that is similar to the smooth look and feel of a filter of a traditional cigarette.

Additionally, the portion of the outer surface 20 of the outer wrapper 12 that is intended to simulate the filter portion of a traditional cigarette may have a layer of non-paper laminate 24 coupled thereto—though it may be desired to not provide such a laminate, for example where the conduit 10 is itself textured and where no outer wrapper 12 is provided. The layer of laminate 24 may be made of plastic, polypropylene, polyethylene terephthalate, or other suitable water resistant material. It may be preferable to include a layer of laminate 24 to this filter portion of the outer surface 20 of the outer wrapper 12 in order to protect the outer wrapper 12 from degrading after coming into contact with saliva from the interior of the user's mouth or if it otherwise comes into contact with moisture. It is preferable that the thickness of the outer wrapper 12 and layer of laminate 24 together will have the same thickness of the outer wrapper 12 and texture layer 22 together. This will help maintain a uniform thickness throughout the length of the entire electronic cigarette 100.

The outer wrapper 12 and texture layer 22 together (and the outer wrapper 12 and laminate 24 together) may have a desired thickness, such as 0.75 mm. However, it should be clearly understood that substantial benefit may be derived from an alternate thickness. For example, the outer wrapper 12 and texture layer 22 (and the outer wrapper 12 and laminate 24) may have a thickness of between 0.5 mm to 3 mm, depending upon the desired outside diameter of the electronic cigarette 100. As a further example, if the electronic cigarette 100 is to be the size of a regular sized traditional cigarette, then the outside diameter of the electronic cigarette 100 may be 8 mm, with the outer wrapper 12 and texture layer 22 (and the outer wrapper 12 and laminate 24) having a total thickness of between about 0.75 mm-1.5 mm.

It should be clearly understood, that substantial benefit may still be derived from an embodiment that does not include a laminate 24 layer. If no laminate 24 layer is used, then the thickness of the portion of the outer wrapper 12 that is intended to simulate the filter portion of a traditional cigarette may have a greater thickness than the portion of the outer wrapper 12 (together with the particulate 26) that is intended to simulate the tobacco rod portion of a traditional cigarette. For example, the outer wrapper 12 and texture layer 22 together (the portion intended to simulate the tobacco rod portion of a traditional cigarette) may have a desired thickness of 0.75 mm and the outer wrapper 12 alone (the portion intended to simulate the filter of a traditional cigarette) may also have a thickness of 0.75 mm. This will allow for the electronic cigarette 100 to have a uniform diameter throughout its entire length.

Figure 5:
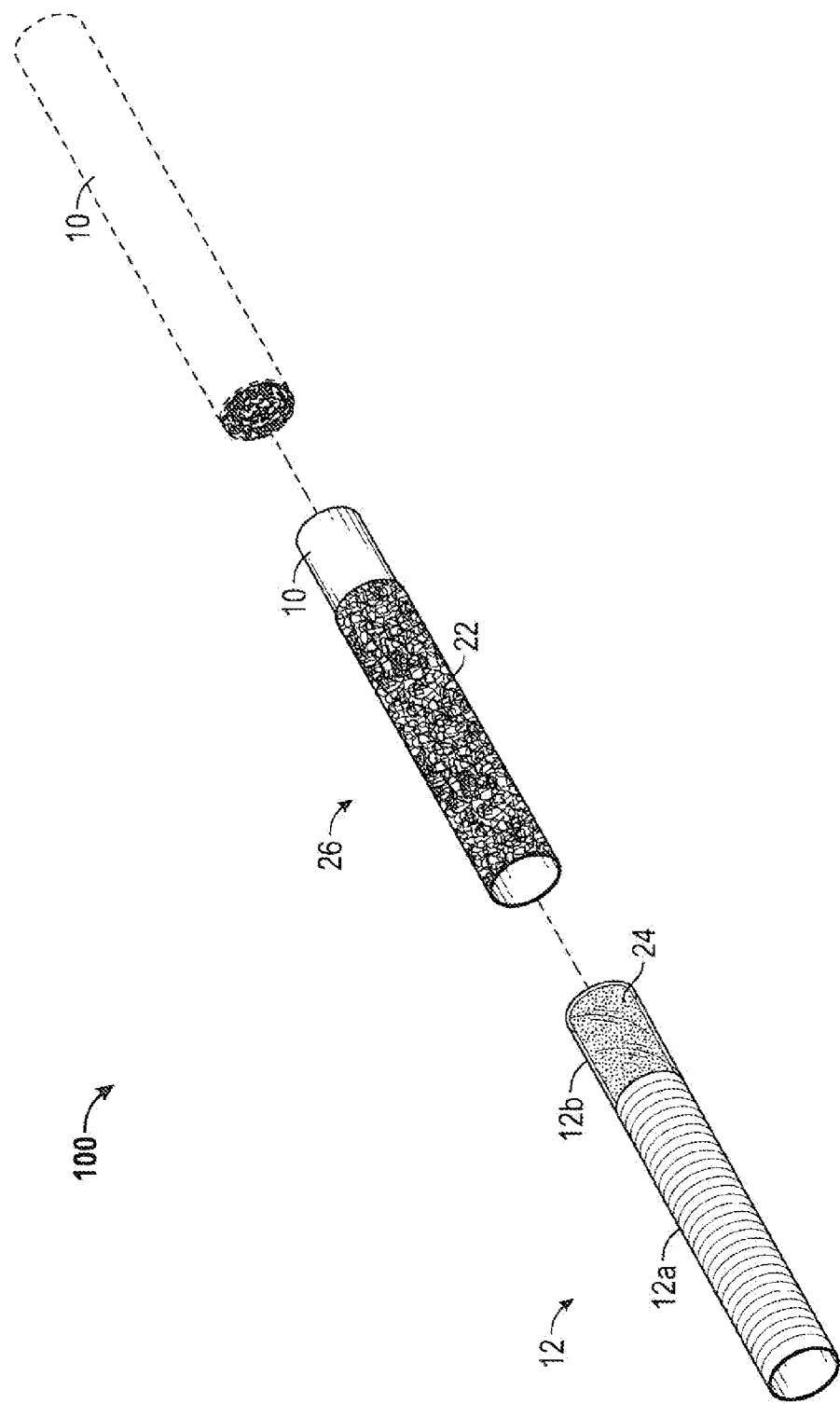
FIG. 5 is an exploded perspective view of the conduit, texture layer, and outer wrapper for another embodiment of an electronic cigarette in accordance with one or more aspects of the present invention.

In another embodiment, shown in FIG. 5, the texture layer 22 may comprise a particulate 26 that is adhered to a portion of the outer surface of the conduit 10; i.e. the portion of the conduit 10 that is intended to replicate the tobacco rod of a traditional cigarette. A suitable amount of particulate 26 may be adhered and layered onto the outer surface of the conduit 10 to achieve a texture layer 22 of a desired thickness. The outer wrapper 12 may then be adhered to the outer surface of the particulate texture layer 22.

Figure 6:
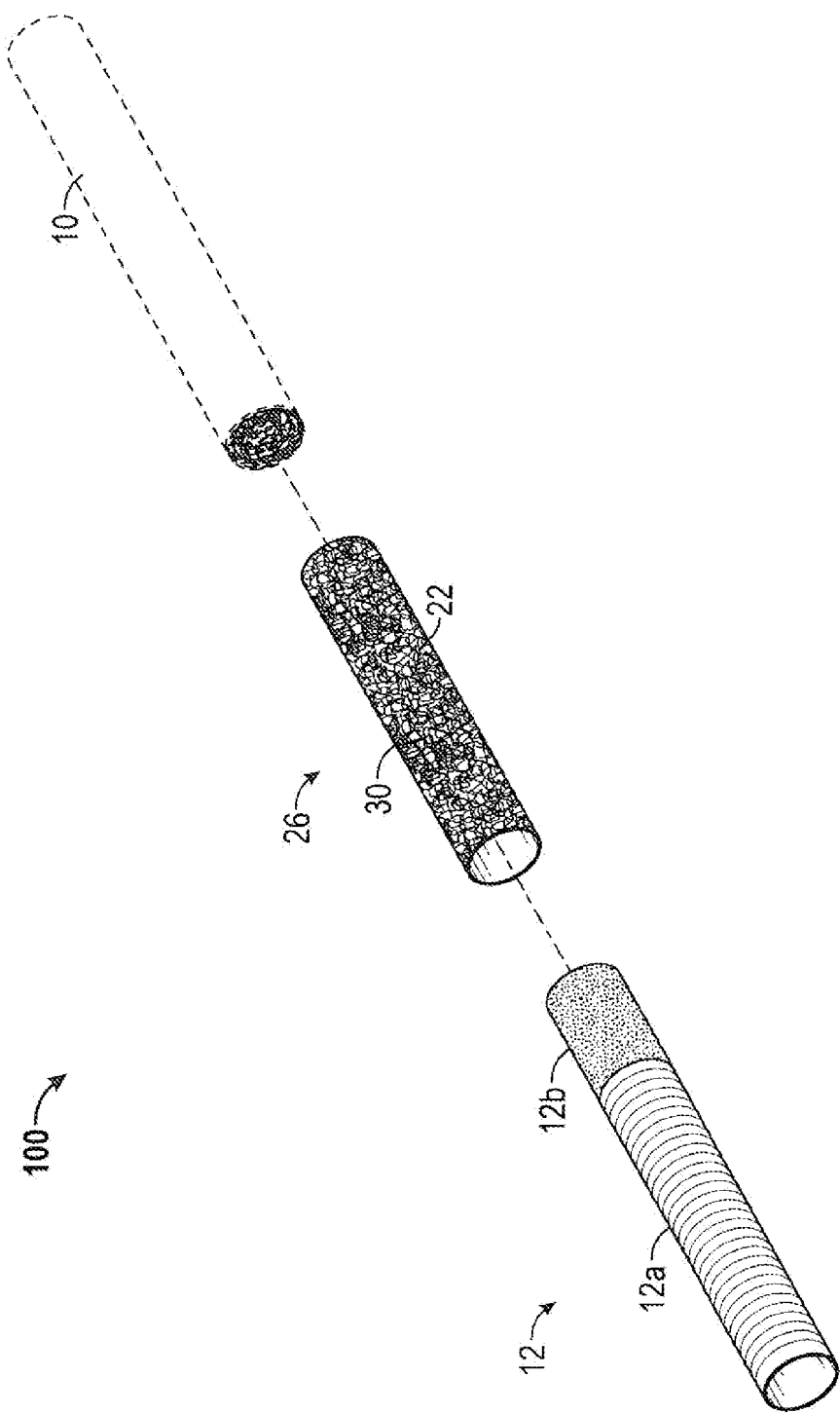
FIG. 6 is an exploded perspective view of the conduit, texture layer, and outer wrapper for another embodiment of an electronic cigarette in accordance with one or more aspects of the present invention.

Referring to FIG. 6, another embodiment of the present invention comprises a texture layer 22 that surrounds the conduit 10 and lies beneath the outer wrapper 12. The texture layer 22 may comprise a synthetic or organic material. As an example, the texture layer 22 may comprise a compressed material, such as paper or some other suitable material that may be compression molded or blow molded so that it is shaped into a sleeve 30 that fits about the conduit 10. The sleeve 30 may have an inner diameter slightly larger than the outer diameter of the conduit 10 so that the sleeve 30 may fit snugly about the conduit 10. The texture layer 22 may also be constructed of polystyrene or some other similar material. The texture layer 22 may also be made of tobacco leaves similar to that used in traditional cigarettes. The texture layer may also be infused with an aroma; e.g. tobacco or menthol scented.

In another embodiment, the internal components (not shown) may be contained directly within the texture layer 22, which effectively functions as both a texture layer 22 and a conduit 10. The outside diameter of the internal components would be slightly less than the inside diameter of the texture layer 22 so that they may be held in place within the texture layer 22 by friction created between the outer surface of the internal components and the inner surface of the texture layer 22. In this embodiment, the texture layer 22 may be constructed of a flexible material that may also be compression molded to simulate the texture of the tobacco rod of a traditional cigarette.

The foregoing description is provided to enable any person skilled in the relevant art to practice the various embodiments described herein. Various modifications to these embodiments will be readily apparent to those skilled in the relevant art, and generic principles defined herein can be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public.

I claim:

1. An electronic cigarette having:
    a conduit that extends the entire length of the electronic cigarette;
    a single outer wrapper coupled to the conduit and adapted to cover the entire length of the conduit, wherein the outer wrapper comprises paper having:
        a first portion configured to simulate cigarette paper wrapped about a tobacco rod portion of a traditional cigarette;
        a second portion configured to simulate a filter portion of a traditional cigarette;
        an overlap portion located along the entire length of an inner surface of the outer wrapper and adjacent to the first portion and second portion;
        a texture layer coupled to an entire inner surface of only the first portion of the outer wrapper, wherein the texture layer comprises a layer of particulate; and
        a laminate layer coupled to an entire outer surface of only the second portion of the outer wrapper;
    wherein the texture layer and the first portion of the outer wrapper together are configured to provide a surface of the electronic cigarette device that is non-smooth to the touch and that simulates a surface of a tobacco rod in a tobacco cigarette; and
    wherein the first portion of the outer wrapper and the texture layer have a combined thickness that is equal to a combined thickness of the second portion of the outer wrapper and the laminate layer.

2. The electronic cigarette device of claim 1 wherein components of the electronic cigarette device are disposed within the conduit.

3. The electronic cigarette of claim 1, wherein a portion of the particulate is embedded into the inner surface of the first portion of the outer wrapper.

4. The electronic cigarette of claim 1 wherein particulate is adhered to an outer surface of the conduit.

5. The electronic cigarette of claim 1 wherein the texture layer comprises a molded sleeve.

6. The electronic cigarette of claim 1 wherein the outer wrapper and the texture layer together have a combined thickness of between approximately 0.5 mm to approximately 3 mm.

7. The electronic cigarette of claim 1 wherein the second portion of the outer wrapper is coupled directly to the conduit.

8. The electronic cigarette of claim 1 wherein the texture layer is infused with a tobacco aroma.

9. An electronic cigarette having:
- a conduit adapted to contain all of the components of an electronic cigarette device;
- an outer wrapper coupled to the conduit and adapted to cover the entire length of the conduit, wherein the outer wrapper comprises paper having:
  - a first portion configured to simulate cigarette paper wrapped about a tobacco rod portion of a traditional cigarette;
  - a second portion configured to simulate a filter portion of a traditional cigarette;
  - an overlap portion located along the entire length of an inner surface of the outer wrapper and adjacent to the first portion and second portion;
  - a texture layer coupled to a distal portion of the conduit and coupled to an entire inner surface of the first portion of the outer wrapper, wherein the texture layer comprises a layer of particulate; and
  - a laminate layer coupled to an entire outer surface of the second portion of the outer wrapper;
- wherein the overlap portion is void of particulate; and
- wherein the first portion of the outer wrapper and the texture layer have a combined thickness that is equal to a combined thickness of the second portion of the outer wrapper and the laminate layer.

10. The electronic cigarette of claim 9 wherein the particulate is embedded into the inner surface of the first portion of the outer wrapper.

11. The electronic cigarette of claim 9 wherein the particulate is adhered to an outer surface of the conduit.

12. An electronic cigarette having:
- a conduit adapted to contain all of the components of an electronic cigarette device;
- an outer wrapper coupled the to the conduit and adapted to cover the entire length of the conduit, wherein the outer wrapper comprises paper having:
  - a first portion configured to simulate cigarette paper wrapped about a tobacco rod portion of a traditional cigarette, the first portion defining an overlap portion along one long edge of the outer wrapper; and
  - a second portion configured to simulate a filter portion of a traditional cigarette, the second portion also further defining the overlap portion along the long edge of the outer wrapper;
  - a layer of particulate coupled to an entire inner surface of the first portion of the outer wrapper except for the overlap portion; and
  - a laminate coupled to an entire outer surface of the second portion of the outer wrapper including the overlap portion,
- wherein the second portion of the outer wrapper is coupled directly to the conduit; and
- wherein the first portion of the outer wrapper and the layer of particulate have a combined thickness that is equal to a combined thickness of the second portion of the outer wrapper and the laminate.

13. The electronic cigarette of claim 12 wherein the first portion of the outer wrapper and the layer of particulate together have a combined thickness of between approximately 0.5 mm to approximately 3 mm and wherein the second portion of the outer wrapper and the laminate together have a combined thickness of between approximately 0.5 mm to approximately 3 mm.

* * * * *